United States Patent [19]

McComb et al.

[11] Patent Number: 4,785,336
[45] Date of Patent: Nov. 15, 1988

[54] DEVICE FOR MONITORING CHARACTERISTICS OF A FILM ON A SUBSTRATE

[75] Inventors: Walter D. McComb, Oregon; Richard D. Schave, Perrysburg; Gregory S. Lee, Bowling Green; Andrew W. Rudolph, S. Elmore, all of Ohio

[73] Assignee: Libbey-Owens-Ford Co., Toledo, Ohio

[21] Appl. No.: 937,741

[22] Filed: Dec. 4, 1986

[51] Int. Cl.$^4$ .............................................. G01B 11/06
[52] U.S. Cl. ...................................... 356/382; 356/405; 356/445; 356/236
[58] Field of Search ............... 356/381, 386, 382, 445, 356/447, 448, 236, 405, 419; 250/228

[56] References Cited

U.S. PATENT DOCUMENTS

| | | |
|---|---|---|
| 3,737,237 | 6/1973 | Zurasky ........................... 356/382 X |
| 3,892,490 | 7/1975 | Vetsuki et al. .................. 356/382 X |
| 3,936,189 | 2/1976 | De Remigis ..................... 356/405 X |
| 4,003,660 | 1/1977 | Christie, Jr. et al. ............ 356/448 X |
| 4,012,144 | 3/1977 | Hedelman ........................ 356/236 X |
| 4,395,126 | 7/1983 | Kramer .......................... 356/236 X |
| 4,479,718 | 10/1984 | Alman ............................. 356/405 |
| 4,606,641 | 8/1986 | Yamada et al. ................. 356/382 X |

FOREIGN PATENT DOCUMENTS 0154602 9/1983 Japan ................................. 356/381

Primary Examiner—Eugene R. LaRoche
Assistant Examiner—Seung Ham
Attorney, Agent, or Firm—Marshall & Melhorn

[57] ABSTRACT

An apparatus for determining and displaying selected characteristics of a film formed on the surface of a glass ribbon includes a scanning head mounted on a track for movement above the filmed surface of the glass ribbon. The scanning head has a source of light pulses generated from a tungsten lamp and chopper, filtered to simulate daylight and focused on the filmed surface. An integrating sphere is also mounted on the scanning head and has an entrance port formed in a wall thereof for collecting a portion of the light being reflected from the surface. Optically filtered detectors mounted in detector ports formed in the wall of the sphere generate output signals representing the "Y" and "Z" components of the collected light on the CIE X,Y,Z, tristimulus scale. A programmed microprocessor is responsive to the detector signals and information concerning the position of the scanning head with respect to the surface of the glass ribbon for generating visual displays of selected characteristics such as reflectivity, b* on the CIELAB tristimulus scale and overcoat thickness as a function of the position at which the light beam is reflected from the filmed surface.

32 Claims, 2 Drawing Sheets

DEVICE FOR MONITORING CHARACTERISTICS OF A FILM ON A SUBSTRATE

BACKGROUND OF THE INVENTION

The present invention concerns monitoring devices for films on substrate surfaces and, in particular, a device for optically determining the characteristics of a thin film on the surface of a glass sheet.

Films are typically applied to glass to either absorb solar radiation or to reflect solar radiation. There are many applications both in industry and in research for an instrument to measure the thickness of thin films. Various devices are available commercially for this purpose. For example, surface profile monitors measure the step size, at a point where the film has been etched through to the substrate, by tracking a stylus over the surface. Physical contact can distort or damage the surface so that a non-contact measurement method is in many cases desired. Methods based on the reflection of light from a film surface offer such a non-contact probe.

There are essentially two distinct techniques for the optical determination of film thickness. The first, known as ellipsometry, measures and compares the reflection coefficient at a given wavelength and an angle to incidence for polarization perpendicular and parallel to the plane of incidence. Considerable computation is required and unambiguous results are obtained only if it is known a priori that the film thickness lies within a restricted range, usually 0 to about 3,000 angstroms. The second class of optical techniques is based on the wavelength and/or angle of incidence dependence of the reflectivity, observable as the well-known interference colors in thin films. Although the principle of this technique is simple, instruments based on this principle are not inexpensive and the simplest instruments do not even provide a direct reading of the film thickness.

An optical thickness gauge that measures the thickness of transparent or semi-transparent sheet material, by the reflectivity technique used in the second class of prior art techniques described above, is disclosed in U.S. Pat. No. 2,655,073. This gauge reflects light from a specimen sheet material onto a rotatable flat optical reflector having parallel surfaces to form interference fringes when the reflected light beams are in phase. The flat optical reflector is rotated in the path of the reflected beam from the specimen beam to the angle at which the light beams are in phase to form the fringes for display on a mirror. The angle of rotation of the reflector is the measure of the thickness of the sheet material. This patent also describes the use of an optical wedge which is utilized to form interference fringes when the reflected beams are in phase wherein the thickness of the optical wedge coincides with the thickness of the specimen.

SUMMARY OF THE INVENTION

The present invention concerns an on-line reflectance monitor for scanning and monitoring characteristics of a glass ribbon such as b*, film side reflectance, and overcoat thickness. A scanning head is mounted for movement across the path of travel of the glass ribbon. The scanning head includes a chopped light source and an integrating sphere. The chopped light source is utilized to render the system immune to ambient light. The integrating sphere has optically filtered detectors for generating signals representing the "Y" and "Z" values of light reflected from the facing surface of the glass ribbon. The "Y" and "Z" signals are inputs to a computer which calculates the values for b* and overcoat thickness. A three channel device plots the values of b*, overcoat thickness and reflectivity. The input data and calculated data are also sent to a larger computer which calculates statistical data and drives other output devices at remote locations.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DESCRIPTION OF THE PREFERRED EMBODIMENT

Figure 1:
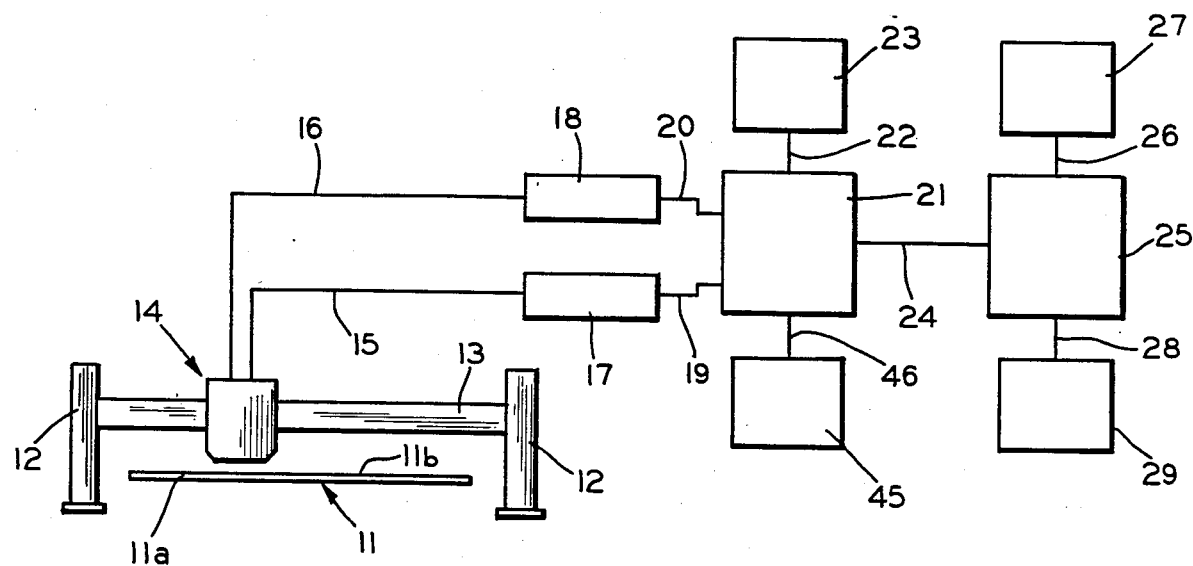
FIG. 1 is a block diagram of an on-line reflectance monitor system according to the present invention.

There is shown in FIG. 1 a block diagram of an on-line reflectance monitoring system according to the present invention. A substrate such as a ribbon of glass 11 being formed by the well known float method is represented as moving toward the observer with a forward or leading edge 11a showing and having an upwardly facing surface 11b upon which a relatively thin film coating has been applied. The glass ribbon 11 passes between a pair of spaced apart vertically extending support posts 12. Extending between the posts 12 is a generally horizontal track 13 upon which is mounted a scanning head 14. The scanning head 14 can be driven back and forth along the track 13 from one side of the glass ribbon 11 to the other side by any well known motive means (not shown).

As will be discussed below, the scanning head 14 generates a pair of electrical signals on output lines 15 and 16 to a pair of optical monitors 17 and 18 respectively. The optical monitors 17 and 18 can each be a model LM-101 manufactured by the Eddy Company of Santa Monica, Calif. Each of the optical monitors 17 and 18 generates an analog output signal on the lines 19 and 20 respectively to a microprocessor 21. The microprocessor 21 converts the analog electrical signals to digital values and utilizes the values to calculate characteristic signal information concerning b* and overcoat thickness for the glass sheet 11. The characteristic signal data or information signals generated by the microprocessor 21 can be sent on a line 22 to an output device such as a three channel strip chart recorder 23 which plots the values of b*, overcoat thickness and reflectivity versus the position at which the measurement was taken on the surface 11b of the glass ribbon 11.

The output data from the microprocessor 21 can also be sent on a line 24 to a computer 25 such as a main frame manufacturing process computer. The computer 25 is typically programmed to collect manufacturing process data and calculate statistical data which is helpful in evaluating the efficiency of the manufacturing process. The computer 25 outputs its data on a line 26 connected to drive a plotter 27 which could be located, for example, in a quality control station or laboratory. Another line 28 can be connected to a second plotter 29 which could be located near the hot end of the glass ribbon production line for monitoring purposes. The number and type of output devices are only limited by the capacity of the computer 25 to operate such devices.

Figure 2:
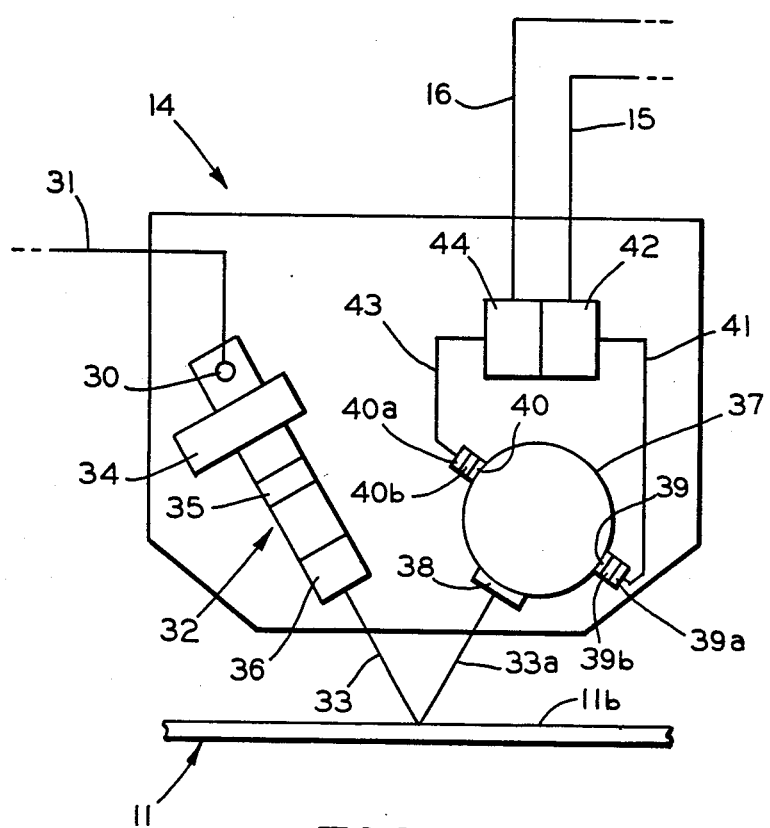
FIG. 2 is an enlarged block diagram of the scanning head shown in FIG. 1.

The scanning head 14 is shown in more detail in schematic form in the block diagram FIG. 2. Carried on the scanning head 14 is a light source 30 which can receive power over an electrical line 31 which can be connected to a power source (not shown). The light source 30 is typically mounted in one end of a housing 32 which emits a beam of light 33 from its other end toward the upper surface 11b of the glass ribbon 11. The housing 32 can include a chopper 34 which functions to interrupt the light beam 33 as it is emitted from the light source 30. The chopper 34 produces a series of pulses of light of a predetermined duration and at a predetermined rate. The light pulses emitted from the chopper 34 pass through a filter 35. Typically the light source 30 is a tungsten lamp which has too large a red color component for the purposes of simulating daylight. A blue filter 35 is utilized to remove some of the red before the pulses of light are focused by a lens 36 mounted in the output end of the housing 32.

The beam of light 33 strikes the upper surface 11b of the glass ribbon 11 at a predetermined angle and is reflected at the same predetermined angle as a beam of light 33a toward an integrating sphere 37 mounted on the scanning head 14. Forty-five degrees is a commonly used value for the angles. The sphere 37 has an entrance port 38 which is aligned with the reflected light beam 33a such that the reflected light enters the interior of the sphere 37. The sphere 37 can be approximately four inches in diameter and the entrance port 38 can be approximately one and three quarters inches in diameter. The size of the entrance port 38 is determined by the amount of available light and the range of distances and angles which can occur between the glass ribbon 11 and the scanning head 14.

The interior of the integrating sphere 37 is coated with a reflecting material and at least two detector ports 39 and 40 are formed in the wall of the sphere 37. Each detector port includes a detector such as a photocell which is responsive to the reflected light inside the integrating sphere 37 for generating an electrical output signal representing the intensity of the light. For example, a detector 39a in the detector port 39 can have its output connected to a line 41 which in turn is connected to the output line 15 through a preamplifier 42. The preamplifier 42 is utilized to boost the magnitude of the detector output signal for subsequent processing by the microprocessor 21. Similarly, a detector 40a in the detector port 40 is connected by a line 43 through a preamplifier 44 to the output line 16.

The CIE (Commission Internationale de l'Eclairage) established several illuminants of known spectral distributions as standards for use in color measurements. Tristimulus colorimetry is based upon the fact that any color can be reproduced by three other colors of controlled amounts. Tristimulus color scales include the X,Y,Z system which represents the ratios of the integrals of light reflected from a sample being measured to the integrals of light reflected from a perfect diffuser, when both are multiplied wavelength by wavelength by the response curve of the Standard Observer and by the Illuminant H. The 1931 CIE Standard Observer response curves define the amount of each of three primary lights (green, amber and blue) needed to reproduce energy of each wavelength from 380 nm to 750 nm wherein the green curve is the standard luminosity curve for the human eye (x is amber, y is green and z is blue).

Each of the photocells can have an optical filter associated therewith for detecting only a predetermined characteristic of the reflected light. For example, the detector port 39 can have an optical filter 39b associated therewith for filtering the light inside the integrating sphere 37 to obtain only the "Z" component thereof. The filter 39b can be a single filter or a combination of two or more filters to obtain the desired results. Similarly, the detector port 40 can have an associated filter 40b for obtaining the "Y" component of the light inside the integrating sphere 37. If the available light inside the sphere 37 is not sufficient to reliably obtain a desired characteristic, an additional detector port, photocell and filter can be added to the integrating sphere and connected to increase the signal magnitude to the associated one of the preamplifiers 42 and 44. Typically a tungsten lamp has too little available energy in the "Z" region and two photocell detectors must be utilized to obtain the proper signal level.

The L,a,b tristimulus system has gained wide acceptance in recent years. L represents the mathematical approximation of the non-linear black-white response of the eye. A perfect white has a value of one hundred and a perfect black has a value of zero. The values of "a" and "b" identify the hue and chroma or color of the sample. A plus value of "a" indicates redness and a minus value indicates greeness. A plus value for "b" indicates yellowness and a minus value indicates blueness. The 1976 CIE L*,a*,b* scale or CIELAB scale has the following relationship with the CIE x,y,z scale:

$$L^* = 116(Y/Y_o)^{\frac{1}{3}} - 16$$

$$a^* = 500((X/X_o)^{\frac{1}{3}} - (Y/Y_o)^{\frac{1}{3}})$$

$$b^* = 200((Y/Y_o)^{\frac{1}{3}} - (Z/Z_o)^{\frac{1}{3}})$$

where $X/X_o$, $Y/Y_o$ and $Z/Z_o$ are each greater than 0.01 and $X_o$, $Y_o$, $Z_o$ define the color of the nominally white object-color stimulus.

Figure 3:
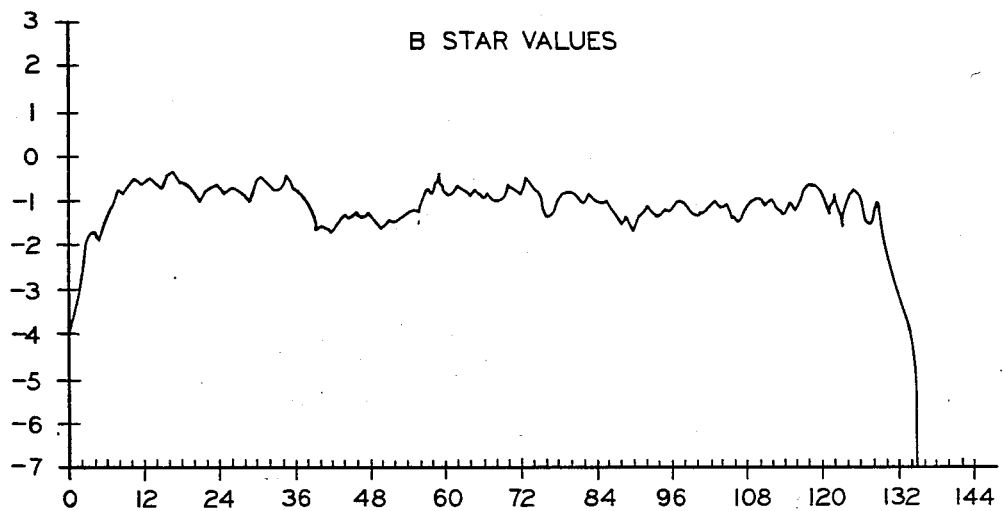
FIG. 3 is a typical plot of b* values obtained utilizing the present invention.

The "Y" signal from the optical monitor 18 and the "Z" signal from the optical monitor 17 are in analog form and are converted to digital form by the microprocessor 21. The microprocessor 21 is programmed to compute the value b* from the formula $b^* = 200((Y/Y_o)^{\frac{1}{3}} - (Z/Z_o)^{\frac{1}{3}})$. "$Y_0$" and "$Z_0$" are reference values which are constant for the equation. The value obtained for b* is then plotted against the position at which the value was obtained on the glass ribbon. The position value can be obtained from a position sensor 45 connected to generate a position signal on a line 46 to the microprocessor 21. Referring to FIG. 3 there is shown such a plot with the values of b* plotted along the ordinate and the location of the scanning head with respect to one side of the glass ribbon plotted in inches along the abscissa. Depending upon the speed of movement of the scanning head 14 and the speed of movement of the glass ribbon 11, the plot of FIG. 3 can represent the values along a line which is essentially perpendicular to the longitudinal axis of the glass ribbon or at some predetermined angle with respect to the longitudinal axis.

Figure 4:
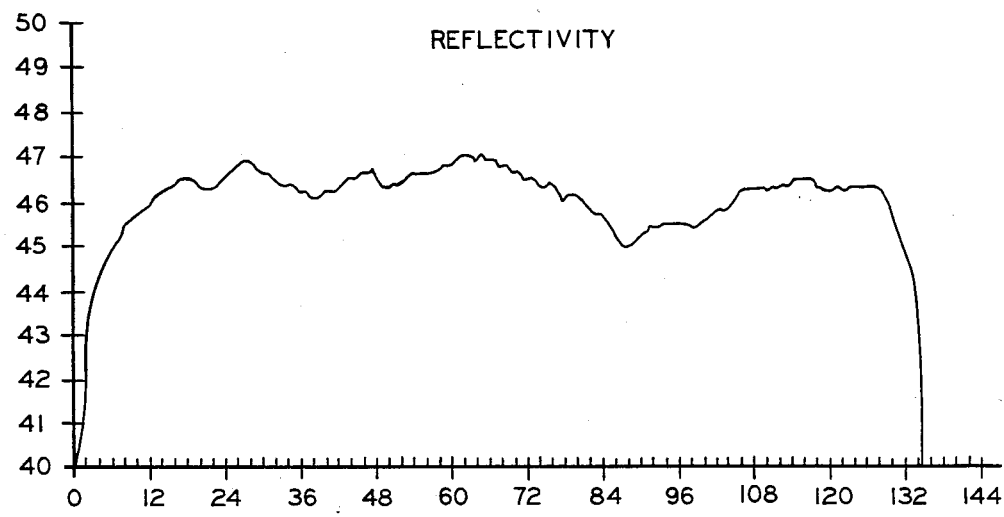
FIG. 4 is a typical plot of reflectivity values obtained utilizing the present invention.

FIG. 4 shows a plot of reflectivity with the reflectivity values along the ordinate and the position of the scanning head along the abscissa. Reflectivity is the "Y" value obtained from the optical monitor 18. As stated above, the tungsten light source is filtered to simulate light in the daylight range. For example, a tungsten lamp with appropriate filter correction can simulate average daylight such as a completely overcast sky which is commonly called the CIE Illuminant C.

Figure 5:
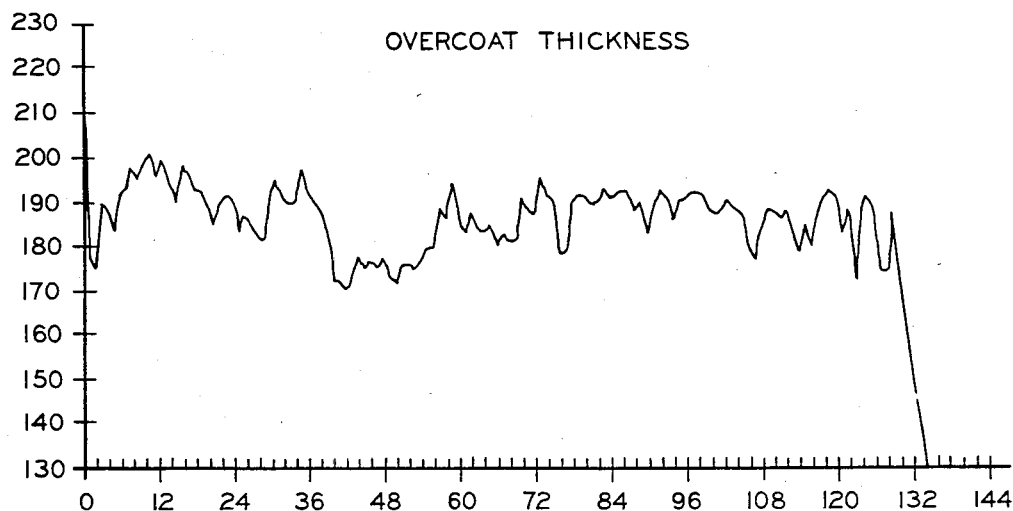
FIG. 5 is a typical plot of overcoat thickness values obtained utilizing the present invention.

FIG. 5 is a plot of overcoat thickness values along the ordinate and the position of the scanner head along the abscissa. Overcoat thickness can be calculated from the values of "Y" and "Z". However, the desired values can be obtained more quickly and with a sufficient degree of accuracy from a lookup table of previously calculated values which are stored in the microprocessor 21. The stored values are referenced to values of "Y" and b*.

The plots shown in FIGS. 3-5 are generated by the computer 25 on one of the output devices which can be graphic display devices such as plotters or printers 27 and 29. The values can be monitored by operating personnel and/or electronically monitored for correcting the manufacturing process should the values become out of range. If the value of b* is too high, the reflected light has too much yellow color. If the value is too low, the reflected light has too much blue color. These measurements are extremely important for architectural glass where multiple windows in a building must be of the same color. If the composition of the glass is such that the value of a* is important, another detector can be installed in the sphere 37 to obtain the "X" component of the light which is required for the calculation of a*.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. An apparatus for determining selected characteristics of a film on a substrate, comprising:
   a scanning head mounted for movement along a generally linear path spaced from a surface of a substrate;
   a source of light attached to said scanning head;
   means for directing a beam of light from said source of light to illuminate the surface of the substrate;
   means attached to said scanning head for collecting at least a portion of said beam of light reflected from the surface including an integrating sphere formed as a hollow ball having an entrance port formed in a wall thereof and oriented toward the substrate surface whereby at least a portion of said beam of light reflected from the surface enters said sphere through said entrance port and is collected in said sphere;
   means responsive to said collected light for generating output signals representing at least two different characteristics of said beam of light; and
   means responsive to said output signals for determining at least one characteristic of a film formed on the surface of the substrate.

2. The apparatus according to claim 1 wherein said scanning head is mounted on a track supported above the surface of the substrate.

3. The apparatus according to claim 2 wherein the substrate is a ribbon of glass and said track is supported at opposite ends by a pair of generally vertically extending supports located on opposite sides of the ribbon.

4. The apparatus according to claim 1 wherein the substrate is formed as a ribbon of material having a longitudinal axis and moving along a path parallel to said longitudinal axis of the substrate and said generally linear scanning head path extends generally perpendicular to said longitudinal axis between opposed sides of said ribbon.

5. The apparatus according to claim 1 wherein said source of light includes a tungsten lamp.

6. The apparatus according to claim 5 wherein said source of light includes a filter for reducing the red color component of said beam of light.

7. The apparatus according to claim 1 wherein said source of light includes chopper means for generating said beam of light as a series of light pulses.

8. The apparatus according to claim 1 wherein said means for directing includes a lens for focusing light from said source of light into said beam of light.

9. The apparatus according to claim 1 wherein an interior surface of said wall of said sphere is coated with a light reflective material.

10. The apparatus according to claim 1 wherein said means for generating output signals includes a detector port formed in said wall of said sphere and a photodetector positioned in said detector port and responsive to said light collected in said sphere for generating one of said output signals.

11. The apparatus according to claim 1 wherein said means for generating output signals includes at least a pair of detector ports formed in said wall of said sphere and first and second photodetectors positioned in respective ones of said detector ports and responsive to said light collected in said sphere for generating first and second ones of said output signals respectively.

12. The apparatus according to claim 11 wherein said means for generating output signals includes first and second optical filter means mounted for filtering said light collected in said sphere and detected by said first and second photodetectors respectively.

13. The apparatus according to claim 12 wherein said first filter means passes said light having a "Y" component value of the CIE X,Y,Z tristimulus scale to said first photodetector and said first output signal represents the intensity of said "Y" component light.

14. The apparatus according to claim 12 wherein said second filter means passes said light having a "Z" component value of the CIE X,Y,Z tristimulus scale to said second photodetector and said second output signal represents the intensity of said "Z" component light.

15. The apparatus according to claim 1 wherein said output signals are in analog form and said means for determining at least one characteristic includes a microprocessor responsive to said output signals for converting said analog form to digital form and for processing said output signals in digital form to generate a characteristic signal and including a display device responsive to said characteristic signal for visually displaying a predetermined characteristic of a film on the substrate.

16. The apparatus according to claim 15 wherein said predetermined characteristic is a value of the CIELAB tristimulus scale.

17. The apparatus according to claim 15 wherein said predetermined characteristic is a value of reflectivity.

18. The apparatus according to claim 15 wherein said predetermined characteristic is a value of thickness of the film.

19. An apparatus for determining characteristics of a thin film formed on a substrate surface, comprising:
   means for generating a beam of light;
   means for directing said beam of light onto a surface of a substrate;
   a hollow integrating sphere having an entrance port formed in a wall thereof, said sphere collecting at least a portion of said light beam reflected from the surface of the substrate;
   means responsive to the light collected in said sphere for generating an output signal representing a characteristic of said collected light an another output signal representing another characteristic of said collected light; and
   means responsive to said output signals for determining a characteristic of a film formed on the surface of the substrate.

20. The apparatus according to claim 19 wherein said means for generating a beam of light includes a tungsten lamp source for generating radiant energy, a chopper for generating said beam of light as a series of light pulses from said radiant energy, and filter means for reducing a red color component of said beam of light.

21. The apparatus according to claim 20 wherein said means for directing includes a lens means for focusing said beam of light onto the surface of the substrate at a predetermined angle.

22. The apparatus according to claim 19 wherein said means for generating an output signal includes a detector port formed in said wall, optical filter means associated with said detector port for passing a portion of said collected light having said characteristic and detector means responsive to said light passed by said optical filter means for generating said output signal.

23. The apparatus according to claim 22 wherein said detector means generates said output signal representing one of a "Y" characteristic and a "Z" characteristic of said collected light on the CIE X,Y,Z tristimulus scale.

24. The apparatus according to claim 19 wherein said means for generating an output signal includes preamplifier means for increasing the magnitude of said output signal.

25. The apparatus according to claim 19 wherein said means for determining a characteristic includes a programmed microprocessor responsive to said output signal for generating an information signal representing the value of said film characteristic and output means responsive to said information signal for generating a visual display of the value of said film characteristic.

26. The apparatus according to claim 25 wherein said detector means generates said output signal representing the value of the "Y" component of said collected light on the CIE X,Y,Z tristimulus scale and said microprocessor generates said information signal representing the value of the reflectivity characteristic of the film.

27. The apparatus according to claim 25 wherein said detector means generates said pair of output signals representing the values of the "Y" and "Z" components of said collected light on the CIE X,Y,Z tristimulus scale and said microprocessor generates said information signal representing the value of the b* characteristic of the film on the CIELAB tristimulus scale.

28. The apparatus according to claim 25 wherein said detector means generates said pair of output signals representing the values of the "Y" and "Z" components of said collected light on the CIE X,Y,Z tristimulus scale and said microprocessor generates said information signal representing the value of the overcoat thickness of the film.

29. The apparatus according to claim 25 wherein said output means is a graphic display device for generating a plot of said film characteristic.

30. The apparatus according to claim 25 wherein said means for determining a characteristic includes position sensor means for generating a position signal representing the position at which said beam of light is reflected from the substrate surface and said output means is responsive to said information signal and said position signal for generating a visual display of the value of said film characteristic plotted against the associated position on the substrate surface.

31. An apparatus for determining selected characteristics of a thin film formed on a glass ribbon substrate, comprising:
   a scanning head mounted for movement along a track positioned above a surface of a glass ribbon being moved in a direction generally parallel to the longitudinal axis of the glass ribbon;
   means for supporting said track above the glass ribbon;
   means mounted on said scanning head for generating a beam of light simulating daylight as a series of light pulses focused on the glass ribbon surface;
   an integrating sphere mounted on said scanning head and having an entrance port formed in a wall thereof for collecting at least a portion of said light beam reflected from the glass ribbon surface;
   a pair of optically filtered detector means mounted in a pair of detector ports formed in said sphere wall and responsive to said collected light for generating a first output signal representing a "Y" component and a second output signal representing a "Z" component of said collected light on the CIE X,Y,Z tristimulus scale; and
   microprocessor means responsive to said first and second signals for generating at least one information signal representing one of the reflectivity, b* on the CIELAB tristimulus scale and overcoat thickness values of a film on the glass ribbon surface.

32. The apparatus according to claim 31 including position sensor means for generating a position signal representing the position at which said beam of light is reflected from the glass ribbon surface and wherein said microprocessor is responsive to said position signal for generating a visual display of the characteristic value represented by said information signal plotted against the position at which said light beam is reflected.

* * * * *

UNITED STATES PATENT AND TRADEMARK OFFICE
CERTIFICATE OF CORRECTION

PATENT NO. : 4,785,336
DATED : November 15, 1988
INVENTOR(S) : Walter D. McComb et al.

It is certified that error appears in the above-identified patent and that said Letters Patent is hereby corrected as shown below:

In the claims:

Column 6, claim 16, line 67, after "of" insert -- b* on --.

Signed and Sealed this

Twenty-first Day of November, 1989

*Attest:*

JEFFREY M. SAMUELS

*Attesting Officer*     *Acting Commissioner of Patents and Trademarks*